US010577639B2

(12) United States Patent
Schultz et al.

(10) Patent No.: US 10,577,639 B2
(45) Date of Patent: Mar. 3, 2020

(54) RAPID BED-SIDE MEASUREMENT OF NEUTROPHIL ELASTASE ACTIVITY IN BIOLOGICAL FLUIDS

(75) Inventors: Gregory S. Schultz, Gainesville, FL (US); Daniel J. Gibson, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 0 days.

(21) Appl. No.: 13/376,508

(22) PCT Filed: Jun. 28, 2010

(86) PCT No.: PCT/US2010/040215
§ 371 (c)(1),
(2), (4) Date: Dec. 16, 2011

(87) PCT Pub. No.: WO2010/151878
PCT Pub. Date: Dec. 29, 2010

(65) Prior Publication Data
US 2012/0135443 A1    May 31, 2012

Related U.S. Application Data

(60) Provisional application No. 61/220,866, filed on Jun. 26, 2009.

(51) Int. Cl.
| | | |
|---|---|---|
| C12N 9/48 | (2006.01) | |
| C12Q 1/37 | (2006.01) | |
| G01N 33/542 | (2006.01) | |

(52) U.S. Cl.
CPC ............. *C12Q 1/37* (2013.01); *G01N 33/542* (2013.01); *G01N 2333/966* (2013.01)

(58) Field of Classification Search
USPC ....................................................... 435/212
See application file for complete search history.

(56) References Cited

U.S. PATENT DOCUMENTS

| | | |
|---|---|---|
| 2005/0153306 A1 | 7/2005 | Harris et al. |
| 2008/0132468 A1 | 6/2008 | Cullen |
| 2009/0136477 A1 | 5/2009 | Nguyen et al. |

FOREIGN PATENT DOCUMENTS

| | | | |
|---|---|---|---|
| WO | WO 03/040406 A2 | 5/2003 | |
| WO | WO 2005/021512 A1 | 3/2005 | |
| WO | WO2010022281 | * 2/2010 | ............... C12Q 1/37 |

OTHER PUBLICATIONS

Korkmaz et al, Measuring elastase, proteinase 3 and cathepsin G activities at the surface of human neutrophils with fluorescence resonance energy transfer substrates. Nat Protoc. May 15, 2008;3(6):991-1000. doi: 10.1038/nprot.2008.63.*
Barrett, Leukocyte Elastase. Methods in Enzymology, vol. 80 (1981) p. 581-588.*
MEROPS, Summary for elastase-2. Downloaded Dec. 13, 2019.*
MEROPS, Ala-Ala clevage by peptidases. Downloaded Dec. 13, 2019.*
Ai et al, Neutrophil elastase in pressure ulcer fluid degrades fibronectin in the exudates. Geriatrics and Gerontology International 2004; 4: 141-45.*
Kainulainen et al, Syndecans, heparan sulfate proteoglycans, maintain the proteolytic balance of acute wound fluids. J Biol Chem. May 8, 1998;273(19):11563-9.*
Rasmussen et al, Use of a Multiple-Enzyme/Multiple-Reagent Assay System to Quantify Activity Levels in Samples Containing Mixtures of Matrix Metalloproteinases. Biochemistry, 2004, 43 (11), pp. 2987-2995.*
Ebell, M. Information at the point of care: answering clinical questions. J Am Board Fam Pract. May-Jun. 1999;12(3):225-35.*
Cheeseman, R.; DiMeo, L., "Fluorescein as a Field-worth Latent Bloodstain Detection System", Journal of Forensic Identification, 1995 45(6), pp. 631-646.*
Powers et al, Peptide Thioester Substrates for Serine Peptidases and Metalloendopeptidases. Methods in Enzylmology V248 (1995) p. 3-18.*
MEROPS database proteases cleaving Ala-Ala↓Ala-Ala. Performed May 2, 2018.*
MEROPS database neutrophil elastase, cleavage specificity. Performed May 2, 2018.*
Iuonut et al, 2011, entitled "Proteases as Biomarkers in Wound Healing" Timisoara Medical Journal No. 1-2, p. 65-73.*
Yager et al, Wound Fluids from Human Pressure Ulcers Contain Elevated Matrix Metalloproteinase Levels and Activity Compared to Surgical Wound Fluids. J Invest Dermatol 107:743-748, 1996.*
Trengove et al, Analysis of the acute and chronic wound environments: the role of proteases and their inhibitors. Wound Repair Regen. Nov.-Dec. 1999;7(6):442-52.*
Metzler, Kinetics with high enzyme concentration. In: Enzymes: The Protein Catalysts of Cells. In: Biochemistry, The Chemical Reactions of Living Cells Second Edition 2001 Harcort/ Academic Press, Inc. New York, NY p. 455-533 (Chapter 9).*
Huang et al, Differential expression of urokinase-type plasminogen activator and plasminogen activator inhibitor-1 in early and late gestational mouse skin and skin wounds. Wound Rep Reg 2002;10:387-396).*
Wu et al, Wnt Signaling Induces Matrix Metalloproteinase Expression and Regulates T Cell Transmigration. Immunity 26, 227-239, Feb. 2007.*
Castillo et al., "Sensitive Substrates for Human Leukocyte and Porcine Pancreatic Elastase: A Study of the Merits of Various Chromophoric and Fluorogenic Leaving Groups in Assays for Serine Proteases", *Analytical Biochemistry*, 1979, vol. 99, pp. 53-64.
Döring, "The Role of Neutrophil Elastase in Chronic Inflammation", *American Journal of Respiratory and Critical Care Medicine*, 1994, vol. 150, Supp. 6, pp. S114-S117.
Edwards et al., "Human neutrophil elastase inhibition with a novel cotton-alginate wound dressing formulation", *Journal of Biomedical Materials Research Part A*, 2003, vol. 66, No. 3, pp. 433-440.
Grinnell et al., "Fibronectin Degradation in Chronic Wounds Depends on the Relative Levels of Elastase, α1-Proteinase Inhibitor, and α2-Macroglobulin", *Journal of Investigative Dermatology*, 1996, vol. 106, No. 2, pp. 335-341.

(Continued)

*Primary Examiner* — Sheridan Swope
(74) *Attorney, Agent, or Firm* — Thomas|Horstemeyer, LLP

(57) ABSTRACT

The subject invention provides novel devices and methods for the detection and quantification of neutrophil elastase activity in biological samples.

7 Claims, 2 Drawing Sheets
Specification includes a Sequence Listing.

(56) References Cited

OTHER PUBLICATIONS

Grinnell et al., "Identification of Neutrophil Elastase as the Proteinase in Burn Wound Fluid Responsible for Degradation of Fibronectin", *Journal of Investigative Dermatology*, 1994, vol. 103, No. 2, pp. 155-161.

Johnson et al., "Nonisotopic DNA Detection System Employing Elastase and a Fluorogenic Rhodamine Substrate", *Analytical Chemistry*, 1993, vol. 65, pp. 2352-2359.

Meldal, "Smart Combinatorial Assays for the Determination of Protease Activity and Inhibition", *QSAR & Combinatorial Science*, 2005, vol. 24, No. 10, pp. 1141-1148.

Partrick et al., "Maximal Human Neutrophil Priming for Superoxide Production and Elastase Release Requires p38 Mitogen-Activated Protein Kinase Activation", *Archives of Surgery*, 2000, vol. 135, pp. 219-225.

Powers, "Reaction of Serine Proteases with Halomethyl Ketones", *Methods in Enzymology*, 1977, vol. 46, pp. 197-208.

Samis et al., "Neutrophil Elastase Clevage of Human Factor IX Generates Activated Factor IX-Like Product Devoid of Coagulant Function", *Blood*, 1998, vol. 92, pp. 1287-1296.

Sklar of al., "A Continuous, Spectroscopic Analysis of the Kinetics of Elastase Secretion by Neutrophils", *The Journal of Biological Chemistry*, 1982, vol. 257, No. 10, pp. 5471-5475.

Trengrove et al., "Analysis of the acute and chronic wound environments: the role of proteases and their inhibitors", *Wound Repair and Regeneration*, 1999, vol. 7, No. 6, pp. 442-452.

Venaille et al., "Epithelial cell damage is induced by neutrophil-derived, not pseudomonas-derived, proteases in cystic fibrosis sputum", *Respiratory Medicine*, 1998, vol. 92, pp. 233-240.

Yager et al., "Ability of chronic wound fluids to degrade peptide growth factors associated with increased levels of elastase activity and diminished levels of proteinase inhibitors", *Wound Repair and Regeneration*, 1997, vol. 5, No. 1, pp. 23-32.

Knight, C. Graham, "Fluorimetric Assays of Proteolytic Enzymes", *Methods in Enzymology*, Jan. 1, 1995, vol. 248, pp. 18-34.

\* cited by examiner

RAPID BED-SIDE MEASUREMENT OF NEUTROPHIL ELASTASE ACTIVITY IN BIOLOGICAL FLUIDS

CROSS-REFERENCE TO A RELATED APPLICATION

This application is a National State Application of International Application Number PCT/2010/040215, filed Jun. 28, 2010; which claims the benefit of U.S. provisional application Ser. No. 61/220,866, filed Jun. 26, 2009, all of which are incorporated herein by reference in their entirety.

BACKGROUND OF THE INVENTION

The rapid and accurate detection of target molecules is critical for many areas of research and medical diagnosis. Important features for a diagnostic technique to be used for the detection of analytes are specificity, speed, and sensitivity. Time constraints and ease of on-site analysis can be major limitations.

Neutrophil elastase is a serine protease that is released from activated human neutrophils and concentrated in neutrophil primary granules. Neutrophil elastases are implicated in disparate pathologies including: acute inflammatory diseases including ARDS (Idle, et al, (1985) Am. Rev. Respire. Ids. 132:1098) and inflammatory tissue damage (Doring, G. 1994, *Am J Respir Crit Care Med.*, 150 (suppl 6):S114-S117), airway inflammation in cystic fibrosis (Venaille, T. J., et al., 1998, *Resp. Med*, 92:233-240), and destruction of pro-healing factors and nascent tissue in chronic, non-healing, wounds (Trengove, N. J. et al. *Wound Repair and Regeneration*, 7 (1999): 442-452; Yager, D. R. et al. *Wound Repair and Regeneration*, 5 (1997): 23-32).

Proteolytic capacity of wound fluids has been demonstrated by several studies to inversely correlate with wound healing. Neutrophil elastase activity has, in particular, been demonstrated to correlate with the capacity for wound fluid to degrade pro-healing growth factors (Edwards, J. V. et al., 2003, *J. Biomed Mater Res Pt A*, 66 (3):433-440; Grinnell and Zhu, 1996, *J. Invest. Dermatol.*, 106:335-341; Grinnell and Zhu, 1994, *J. Invest. Dermatol.*, 103:155-161).

Currently, there are no bed-side assays that measure the neutrophil elastase activity. Current assay systems are time, skill, and price intensive. Thus, a system that would decrease the skill level, time, and equipment necessary to run the assay and permit it to be run at the patient's bedside is needed.

BRIEF SUMMARY OF THE INVENTION

The present invention provides diagnostic methods and devices that can be used to assay a medium, such as tissue in vivo or a sample in vitro, in order to determine the presence and/or quantity of neutrophil elastase.

The proteases detected according to the subject invention are biochemical markers of health that can be used to direct therapy or prophylaxis. Thus, the devices and methods of the invention are of great benefit when diagnosing (and implementing a treatment for) a pathological condition that has one or more of these markers.

For example, a non-healing (chronic) wound is marked by the imbalance of several biological regulators, such as proteases, and protease inhibitors. In preferred embodiments exemplified herein, the subject invention provides assays for the quantification of neutrophil elastase activity at the site of a wound.

In a specific embodiment exemplified herein, the subject invention provides a rapid and accurate assay for quantitatively assessing the presence of one or more neutrophil elastases in a sample taken from a wound. Specifically exemplified herein is a FRET assay that is able to quickly and accurately assess the quantity of neutrophil elastase activity in a sample taken from a wound.

Advantageously, in certain embodiments, the subject invention provides assays that can be self-contained in a single unit. This facilitates conducting assays in the field and, in the case of healthcare, at the point of care.

In an embodiment that is specifically exemplified herein, the subject invention provides assays that can be used to determine and/or monitor the status of a wound, thereby facilitating the administration of appropriate care and treatment. The assays are quick and easy-to-use. In specific embodiments the assay can be carried out by, for example, a nurse utilizing either no instrumentation, or only minimal, instrumentation. In one embodiment, information about the status of a wound can be readily, easily and reliably generated in 10 minutes or less. Information about the wound can include, but is not limited to, neutrophil elastase presence and/or activity. Particularly preferred assays as described herein include, substrate cleavage assays.

Specifically exemplified herein is the use of FRET assays.

Upon conducting the simple procedures of the subject invention, a physician has very important information to treat a condition in an as-needed manner. This information can also be used to design and justify subsequent and related treatments as required by the majority of insurance corporations. The assays of the subject invention can also be used prior to the application of pharmaceutical agents and/or grafts to ensure that the recipient site is conducive to the therapy (e.g. any tissue or protein applied to the site will not be adversely affected by the presence of proteases).

BRIEF DESCRIPTION OF SEQUENCE LISTING

Figure 1:
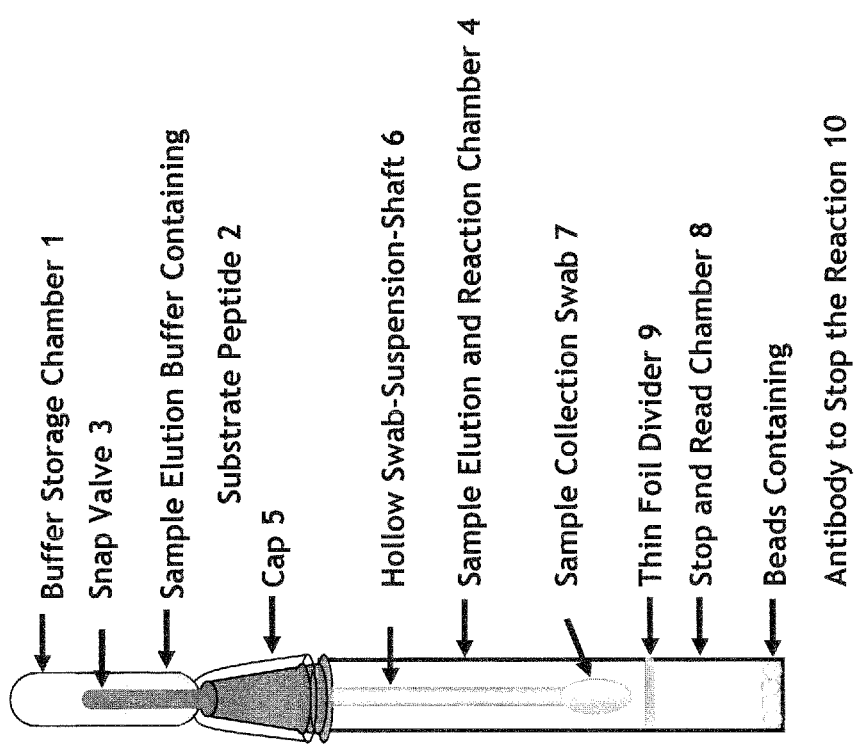
FIG. 1 shows a FRET assay device of the subject invention.

SEQ ID NO:1 is a peptide sequence of a fluorescing dye and quencher-labeled peptide that contains a cleavage site for neutrophil elastases in accordance with the invention.

SEQ ID NOS:2-4 are peptide sequences of fluorophore-labeled peptides, wherein each peptide contains a cleavage site for neutrophil elastases in accordance with the invention.

SEQ ID NOS:5-27 are peptide sequences of fluorescing dye and quencher-labeled peptides, wherein each peptide contains a cleavage site for neutrophil elastases in accordance with the invention.

DETAILED DESCRIPTION OF THE INVENTION

The present invention provides diagnostic methods and devices for detecting neutrophil elastases in a sample. The sample may be, for example, an in vivo tissue sample or an in vitro sample (e.g., biological sample or environmental sample). The method and devices disclosed herein can be used to determine the quantity of one or more target proteases, including neutrophil elastases.

The assays of the subject invention can be used as part of a program to optimize (or at least improve) treating and/or routing in a hospital. In a preferred embodiment, the assays of the subject invention are used to measure the level of neutrophil elastase present in a wound.

Advantageously, in certain embodiments, the subject invention provides assays that can be self-contained in a single unit. This facilitates conducting assays in the field and, in the case of healthcare, at the point of care.

The neutrophil elastase assay of the subject invention is particularly advantageous because, through the careful selection of various parameters, including the substrates, fluorophore and quenchers, the assay exhibits rapid kinetics with excellent accuracy and minimal background interference.

In an embodiment that is specifically exemplified herein, the subject invention provides assays that can be used to determine and/or monitor the status of a wound. The assays are quick and easy-to-use. In specific embodiments, the assay can be carried out by, for example, a nurse utilizing either no instrumentation or only minimal instrumentation. In one embodiment, information about the status of a wound can be readily, easily and reliably generated in 30 minutes or less. In a preferred embodiment, the results are obtained in 15 minutes or less. Most preferably, the results are generated in 10 minutes or less. Information about the wound can include, but is not limited to, neutrophil elastase activity and/or presence.

With regard to protease activity, the activity of neutrophil elastase is of particular interest in wound care. In a specific embodiment, the assays of the subject invention are utilized to assess the status of chronic wounds by determining the quantity of neutrophil elastase present in the wound. As used herein, reference to "chronic wounds" refers to wounds that after 2 weeks are not healing properly.

A variety of assay formats can be used according to the subject invention. Particularly preferred assays as described herein include FRET assays. Preferably, the assays are substrate cleavage assays.

The subject invention also provides sample collection methodologies which, when combined with the assays of the subject invention, provide a highly advantageous system for analyte evaluation in a wide variety of settings. In one embodiment, a "swab-in-a-straw" collection and assay system can be utilized as described herein. The sample can be collected with a Dacron swab with a hollow shaft, which is in communication with a "snap valve" that temporarily separates the swab's hollow center. The center has a reservoir containing the FRET peptide dissolved in a suitable buffer at a concentration dictated by the desired assay time frame and a desired dynamic range.

Due to their ability to easily, quickly and accurately determine the quantity of neutrophil elastase, the devices and methods of the invention facilitate medical diagnoses. at a physician's office and/or at the bedside of the patient. Ex vivo analysis of bodily fluids utilizing a device and method of the invention can be applied to a wide range of diagnostic tests. Analysis of bodily fluid samples using a device or method of the present invention can enable timely interventions for time-sensitive conditions or diseases.

The devices and methods of the invention can also be used for ocular applications, e.g., to assess the presence of ocular infection or molecules that are of diagnostic value in assessing infected and/or inflamed eyes.

The devices and methods of the invention can be used for pulmonary applications, e.g., to assess molecular risk factors for cystic fibrosis. The molecule(s) targeted for detection and/or measurement can be molecules known to be associated with airway, such as neutrophil elastases.

The devices and methods of the invention can be used for dermal applications, e.g., to assess the presence of analytes in tissue or wound fluids that are of diagnostic value in assessing wound healing. The molecule(s) targeted for detection and/or measurement can be, for example, neutrophil elastase activity.

Optionally, in the various embodiments of the invention, the diagnostic method further comprises comparing the concentration of the target molecule in the medium (e.g., a bodily fluid), as determined above, to pre-existing data characterizing the medium (e.g., concentration of the same target molecule in the same patient or a different patient). The target molecule concentration may be that specific target molecule concentration observed under particular conditions.

Optionally, the method of the invention further comprises monitoring the presence and/or concentration of a neutrophil elastase in a medium over a period of time.

Simple "mix-and-read" assays minimize time and increase productivity; assays can be for naked eye or quantitative assessment using well established, relatively inexpensive detection technologies; and an easy-to-interpret detection system when used by non-technical personnel. Advantageously, less equipment and fewer lab skills are necessary to conduct the assays.

Therefore, the subject invention provides bed-side methods and devices for clinicians to monitor a wound's neutrophil elastase activity and/or the wound's response to treatment. Additionally, the methods and devices can be used to determine whether the wound bed is adequately prepared prior to administration of, for example, peptide and protein growth factor based therapies both as a measure of the likelihood that the wound would be responsive to the factors (i.e., that the cell surface receptors are likely still intact) and to ensure that the therapeutics will not be rapidly degraded. The subject invention can also be used to measure the effectiveness of other elastase modulating therapies.

Assays that can be used according to the subject invention to assay for neutrophil elastase activity include assays based on specific cleavage of a substrate and, optionally, separation of a product. These assays may be, for example, FRET assays.

Examples of assay formats are discussed in more detail below.

Substrate Cleavage Assays

The enzymatic activity of neutrophil elastases can be determined using substrate cleavage assays wherein a proteolytic activity of the sample is determined by monitoring the cleavage of a model peptide introduced into the sample.

The substrate is a natural or synthetic peptide sequence having a generic or highly enzyme-specific sequence which is kinetically selective for neutrophil elastase. As such, the degree of enzyme specificity can be tuned to monitor the activity of neutrophil elastase. For example, inhibitors of metalloproteinases or other sieve proteases can be included to improve specificity of the neutrophil elastase. Such inhibitors include, but are not limited to: AEBSF-HCl; Amastatin-HCl; Antipain-HCl; (alpha)1-Antitrypsin from human plasma ((alpha)1-proteinase inhibitor); APMSF-HCl (4-Amidophenyl-methane sulfonyl-fluoride); Aprotinin; DFP (diisopropylfluorophosphate); EDTA; EGTA; Elastatinal; Leupeptin-hemisulfate; PMSF (phenylmethyl sulfonyl fluoride); tosyl-lysyl-chloromethyl ketone (TLCK); and 1-chloro-3-tosylamido-4-phenyl-2-butanone (TPCK). Tethered to the substrate sequences are dye subunits, which may be composed of single or multiple (e.g. dendritic, oligomeric, etc.) dye molecules conjugated to the free end of the substrate.

FRET Assays

The basis of the FRET assay is to bring a fluorescing dye close enough to a dye that prevents fluorescence (quencher) by coupling the dyes to a peptide that is a substrate for the analyte protease. In a specific example, the DABCYL absorbs the color that EDANS fluoresces thereby preventing its detection. Once the protease has severed the peptide the fluorescing dye can now separate far enough away from the quencher to produce a detectable signal.

The peptide joining the dye and quencher can be modified to produce specificity for the protease being measured.

In addition to quenching, FRET can be used to cause a change in fluorescing color. An example is when a green fluorescing molecule is close to a red fluorescing molecule. If a green-exciting light (i.e. blue) is introduced, the green fluorescence is the source of green light to excite the red fluorophore. When they drift, the green light can escape and not be a source of excitation for the red fluorophore. This is an example of a visually interpretable assay (i.e. red to green shift). In a related embodiment, red-fluorescing molecules to be used in accordance with the subject invention include, but are not limited to, Texas-Red, tetramethyl rhodamine, and xanthine-based dyes with red fluorescent emission spectrum.

In general, the mechanics for the quenching can vary depending on the dye and quencher combination, but the concept at the technological level remains the same. Once the peptide is cleaved the EDANS can separate far enough away from the DABCYL for the fluorescent color to escape and be detected.

Typically, a sample that may contain the protease of interest is mixed with these peptides. The sample can then be irradiated, preferably with non-ionizing electromagnetic radiation. The reactions are continuously monitored by a fluorimeter for a change in fluorescent intensity. The products can be quantified by measuring the fluorescence of a known quantity of the dye, and then scaled by the difference in fluorescence between free dye and the peptide fragment bound dye.

Advantageously, in one embodiment, the specificity for these assays is enhanced by the choice of a soluble peptide substrate that is specifically cleaved by neutrophil elastase. The output from this assay can be one or more of the following:
a. LED or filtered white light excitation
  i. UV LED (≤380 nm) for blue-fluorescing fluorophores, and for most fluorophores in general (Blue, most others)
  ii. Blue/Cyan LED (450-495 nm) for green-fluorescing based fluorophores
    (Green/yellow)
  iii. Green LED (540-560 nm) for red-fluorescing fluorophores (Red)
  iv. Red LED (582 nm) for infrared read out
b. Read either by eye or with fluorimeter
  i. Eye
1. Yes/No
2. Semiquantitative scale
  a. Similar to pool chemistry where color/opacity scale is provided for comparison
  ii. Fluorimeter
1. Quantitative via any available photon counting elements
  a. CMOS-based
  b. CCD-based
  c. Photodiode-based
  d. Photoresistor-based Advantageously, due to the narrow spectrum used to excite the dyes, interference due to visibly colored agents (such as hemoglobin) is effectively circumvented. For instance, with fluorescein excitation via blue light, the hemoglobin cannot be seen because it does not scatter/reflect blue light.

Another embodiment of the invention is a device for use in a FRET assay that utilizes chemilumenescent excitation (2,4-Dinitrophenyl oxalate via $H_2O_2$, for example) of the fluorophore upon cleavage. Advantageously, this makes the FRET assay an instrument free assay.

The following examples illustrate procedures for practicing the invention. These examples should not be construed as limiting. It will be apparent to those skilled in the art that the examples involve use of materials and reagents that are commercially available from known sources, e.g., chemical supply houses, so no details are given respecting them.

Example 1—Fret Assay Device

FIG. 1 shows an embodiment of a device of the subject invention based on a FRET assay format.

In one embodiment, the subject invention provides methods and devices for rapid and accurate, quantitative and/or qualitative, measurement of neutrophil elastase by utilizing a FRET assay format.

As shown in FIG. 1, an embodiment of the invention is in the form of a device that can comprise various components including, for example, (1) a buffer storage chamber, (2) elution buffer, containing a peptide substrate, (3) a snap valve, (4) an elution and reaction chamber, (5) a cap separating the buffer storage chamber and the reaction chamber, (6) a hollow swab-suspension shaft, (7) a sample collection swab, (8) a stop and read chamber containing serine protease inhibitors (SERPINS) and/or neutrophil elastase neutralizing antibodies, (9) a thin foil divider separating the elution and reaction chamber and the stop and read chamber, wherein the SERPINS and/or neutrophil elastase neutralizing antibodies are provided in beads (10).

In one embodiment, the hollow swab-suspension shaft comprises a hollow straw and a cotton swab, and the hollow straw comprises the buffer storage chamber and the swab.

This assay can be practiced in the following steps, (1) apply the swab to a sample (such as wound debridement) and collect fluid (such as wound fluid) sample; (2) pull the snap valve to release elution buffer containing peptide substrate. As elution buffer drains down the straw to perfuse the swab, (wound) sample is eluded from the swab, making neutrophil elastases in (wound) fluid available to peptide substrate for proteolysis; (3) wait for the proteolysis reaction; (4) push down the swab to perforate the thin foil divider, allowing the reaction mixture into the stop and read chamber (the anti-protease antibody binds to the protease and stops the reaction); (5) insert the entire device into a fluorimeter to read the result.

Figure 2:
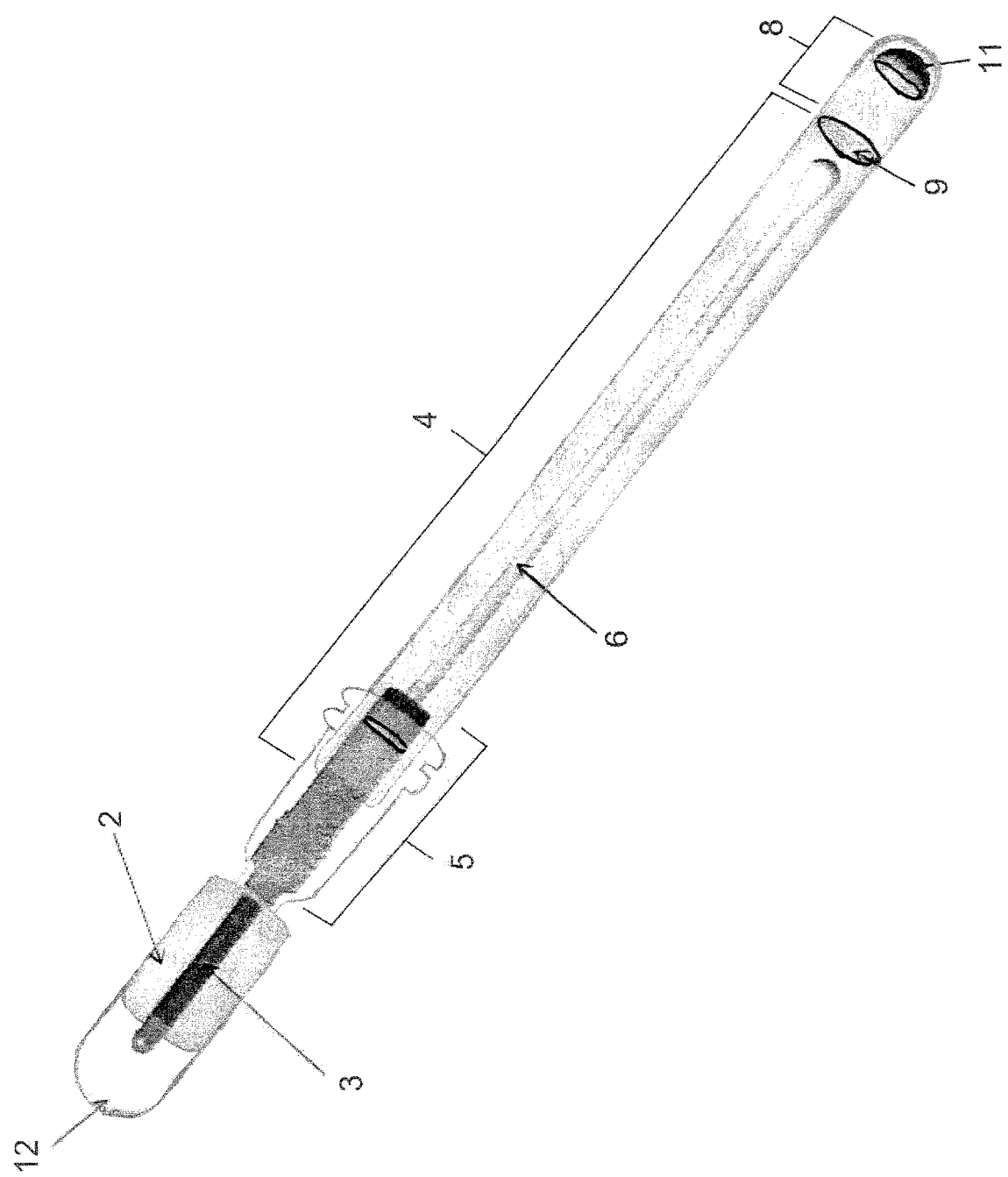
FIG. 2 shows an alternate embodiment of a FRET assay device of the subject invention.

An alternate embodiment is illustrated in FIG. 2. Another form of a device of the invention can comprise: (1) a buffer storage chamber in the form of a squeeze bulb, (2) elution buffer, containing a peptide substrate, (3) a snap valve, (4) an elution and reaction chamber, (5) a cap separating the buffer storage chamber and the reaction chamber, (6) a hollow swab-suspension shaft, (7) a sample collection swab, (8) a stop and read chamber containing serine protease inhibitors (SERPINS) and/or neutrophil elastase neutralizing antibodies, (9) a thin foil divider separating the elution and reaction chamber and the stop and read chamber, wherein the SERPINS and/or neutrophil elastase neutralizing antibodies are provided in solution (11).

In use, the assay of FIG. 2 can be practiced in the following steps, (1) apply the swab to a sample (such as wound debridement for wound fluid sample); (2) pull the snap valve to release elution buffer containing peptide substrate. Squeeze buffer storage chamber to force elution buffer down the hollow swab-suspension shaft to perfuse the swab. Sample obtained on the sample collection swab is eluded from the swab, making neutrophil elastases in sample fluid available to peptide substrate for proteolysis; (3) wait for the proteolysis reaction; (4) push down the swab to perforate the thin foil divider, allowing the reaction mixture into the stop and read chamber (the anti-protease antibody binds to the protease and stops the reaction); (5) insert the entire device into a fluorimeter to read the result.

In certain embodiments, the elution buffer can include free fluorophore (or unattached fluorophore). The concentration of the free fluorophore in the elution buffer is below that fluorimeter's sensitivity to the fluorophore. Preferably, the concentration of the free fluorophore is close to but below the fluorimeter's sensitivity to the fluorophore. This will enable the initial signal generating events (as described above) to be immediately detected and effectively increases a device's sensitivity while shortening the device's minimal readout time.

The peptide substrate can be a fluorophore-labeled soluble peptide, containing a fluorescing dye, a quencher in proximity to the fluorescing dye, and a protease cleavage site between the fluorescing dye and the quencher.

In one embodiment, the peptide substrate contains a cleavage site for neutrophil elastases, to indicate when neutrophil elastase activity levels are elevated in samples of wound fluid.

In a specific embodiment, the peptide sequence is DAB-CYL-Ala-Ala-Pro-Val (SEQ ID NO:1)-(5-FAM). Dabcyl is coupled to the N-terminal and 5-FAM is coupled to the C-terminal of the peptide of SEQ ID NO:1.

The FRET receiver dye is Dabcyl and the fluorophore is 5-carboxyfluorescein (5-FAM).

Other combinations of quencher and fluorophore can be used. One embodiment uses a dual fluorescein pair (both fluorophore and quencher). The advantage of this is having two fluorophores per cleavage. Another specific option is to utilize a fluorescein/rhodamine pair. This results in a change in fluorescence color with cleavage.

Other embodiments include the use of variants of fluorescein (e.g. 5 FAM, 6 FAM, and regular fluorescein) or other xanthene fluorophores (rhodamines, etc).

For any amino acid that possesses at least one free primary amine, the following fluorescein-based molecules can be used to produce comparable results: 5-fluorescein isothiocyanate (5-FITC), 6-fluorescein isothiocyanate (6-FITC), or 5/6-FITC mixed isomers, 5-carboxyfluoroscein (5-FAM), 6-carboxyfluorescein (6-FAM), 5/6-FAM mixed isomers, 5-carboxyfluorescein N-hydroxysuccinimidyl ester (5-fluorescein-SE), 6-carboxyfluorescein N-hydroxysuccinimidyl ester (6-fluorescein-SE), or 5/6-fluorescein-SE mixed isomers.

For amino acids that possesses at least one free carboxylic acid, then any fluorescein derivatized with a primary amine can be used.

For any amino acid that possess at least one free sulfhydryl group, 5-maleimide fluorescein (5-MF), 6-maleimide fluorescein (6-MF), or 5/6-MF mixed isomers, 5-iodoacetamidofluorescein (5-IAF), 6-iodoacetamidofluorescein (6-IAF), or 5/6-IAF mixed isomers can be used.

Finally, rhodamine 110 can be used because it is 1) green fluorescent (i.e. similar spectral characteristics) and 2) a xanthene dye (i.e. similar shape).

Other peptides that can be used include, but are not limited to, MeO-Suc-Ala-Ala-Pro-Val (SEQ ID NO:2)-MCA, Ac-Ala-Ala-Ala-ONp, (Z-Ala-Ala)2-R110 or (Z-Ala-Ala-Ala)2-R110, aka Z-Ala-Ala-Rh110-Ala-Ala (SEQ ID NO:3)-Z or Z-Ala-Ala-Ala-Rh110-Ala-Ala-Ala-Ala (SEQ ID NO:4)-Z, where MeO-Suc represents methylsuccinyl; MCA represents 4-methylcoumarinyl-7-amide; ONp represents p-nitrophenylester; Z represents carbobenzoxy; and Rh110 represents rhodamine 110.

See for example, Sklar, L. A., McNeil, V. M., Jesaitis, A. J., Painter, R. G., and Cochrane, C. G. (1982) A continuous, spectroscopic analysis of the kinetics of elastase secretion by neutrophils. The dependence of secretion upon receptor occupancy, *J Biol Chem* 257, 5471-5475, Castillo, M. J., Nakajima, K., Zimmerman, M., and Powers, J. C. (1979) Sensitive substrates for human leukocyte and porcine pancreatic elastase: a study of the merits of various chromophoric and fluorogenic leaving groups in assays for serine proteases, *Anal Biochem* 99, 53-64, Powers, J. C. (1977) Reaction of serine proteases with halomethyl ketones, *Methods Enzymol* 46, 197-208, Rothe, G., Klingel, S., Assfalg-Machleidt, I., Machleidt, W., Zirkelbach, C., Banati, R. B., Mangel, W. F., and Valet, G. (1992) Flow cytometric analysis of protease activities in vital cells, *Biol Chem Hoppe Seyler* 373, 547-554, Johnson, A. F., Struthers, M. D., Pierson, K. B., Mangel, W. F., and Smith, L. M. (1993) Nonisotopic DNA detection system employing elastase and fluorogenic rhodamine substrate, *Anal Chem* 65, 2352-2359.

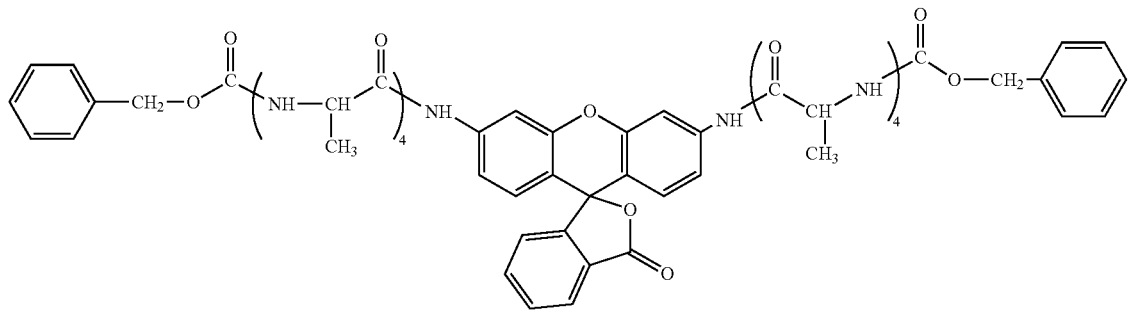

bis(N-benzyloxycarbonyl-L-tetraalanyl)rhodamine
[or (Cbz-Ala4)2-Rhodamine; (BZTAlaR)]

When one or both of the peptides is/are cut the Rhodamine 110 fluorophore is unquenched.

This peptide can be used, as well as a variant there of, with changes including, but not limited to substituting DABCYL for Cbz and/or using only a single peptide system such as: DABCYL-Ala-Ala-Ala-Ala(SEQ ID NO:5)-(5-FAM) and/or DABCYL-Ala-Ala-(5-FAM) so that the quencher/fluorophore system is common across a product line. As understood by the skilled artisan, Dabcyl is coupled to the N-terminal and 5-FAM is coupled to the C-terminal of SEQ ID NO:5. A code, which could be a colored component of the straw (the snap-valve for instance), could differentiate the numerical readout. An example could be: blue-1400 as a signal for elastase with a level of 1400 versus purple-2100 which could be a MMP level of 2100 versus Red-1000 which could be a nitric oxide metabolites level of 1000.) Such a system with common fluorophores can be calibrated such that all devices provide a signal within a common reaction time and within a common dynamic range allowing easier adoption in the clinic due to decreased provider training and a common readout system.

Further peptides that can be used, in which Dabcyl is coupled to the N-terminal of a peptide containing a cleavage site for neutrophil elastases and 5-FAM is coupled to the C-terminal, include but are not limited to:

```
DABCYL-Lys-Ala-Ala-Pro-Val (SEQ ID NO: 6)-(5-FAM)

DABCYL-Arg-Ala-Ala-Pro-Val (SEQ ID NO: 7)-(5-FAM)

DABCYL-GABA-Ala-Ala-Pro-Val (SEQ ID NO: 8)-(5-FAM)

DABCYL-Ala-Ala-Pro-Val-Glu (SEQ ID NO: 9)-(5-FAM)

DABCYL-Ala-Ala-Pro-Val-Asp (SEQ ID NO: 10)-(5-FAM)

DABCYL-Lys-Ala-Ala-Pro-Val-Glu (SEQ ID NO: 11)-(5-
FAM)

DABCYL-Arg-Ala-Ala-Pro-Val-Glu (SEQ ID NO: 12)-(5-
FAM)

DABCYL-GABA-Ala-Ala-Pro-Val-Glu (SEQ ID NO: 13)-
(5-FAM)

DABCYL-Lys-Ala-Ala-Pro-Val-Asp- (SEQ ID NO: 14)(5-
FAM)

DABCYL-Arg-Ala-Ala-Pro-Val-Asp- (SEQ ID NO: 15)(5-
FAM)

DABCYL-GABA-Ala-Ala-Pro-Val-Asp- (SEQ ID NO: 16)
(5-FAM)

DABCYL-Lys-Ala-Ala-Ala-Ala- (SEQ ID NO: 17)(5-FAM)

DABCYL-Arg-Ala-Ala-Ala-Ala- (SEQ ID NO: 18)(5-FAM)

DABCYL-GABA-Ala-Ala-Ala-Ala- (SEQ ID NO: 19)(5-
FAM)

DABCYL-Ala-Ala-Ala-Ala-Glu- (SEQ ID NO: 20)(5-FAM)

DABCYL-Ala-Ala-Ala-Ala-Asp- (SEQ ID NO: 21)(5-FAM)

DABCYL-Lys-Ala-Ala-Ala-Ala-Glu- (SEQ ID NO: 22)(5-
FAM)

DABCYL-Arg-Ala-Ala-Ala-Ala-Glu- (SEQ ID NO: 23)(5-
FAM)

DABCYL-GABA-Ala-Ala-Ala-Ala-Glu- (SEQ ID NO: 24)
(5-FAM)

DABCYL-Lys-Ala-Ala-Ala-Ala-Asp- (SEQ ID NO: 25)(5-
FAM)

DABCYL-Arg-Ala-Ala-Ala-Ala-Asp- (SEQ ID NO: 26)(5-
FAM)

DABCYL-GABA-Ala-Ala-Ala-Ala-Asp- (SEQ ID NO: 27)
(5-FAM)
```

According to the subject invention, one or more Dabcyl receiver dye(s) can be coupled to the N-terminal (depending on the amino acid present) and/or one or more 5-FAM fluorophore(s) can be coupled to the C-terminal of the peptides of the invention. For example, where the peptide sequence at the N-terminus has either lysine, arginine or γ-aminobuteric acid (GABA), both amines located on these amino acids can be labeled with Dabcyl. Also, where the peptide sequence at the C-terminus has either glutamic or aspartic acid, both carboxylic acids located on these amino acids can be labeled with 5-FAM. Examples of peptides of the invention in which two Dabcyl receiver dyes and/or two 5-FAM fluorophores are coupled to a peptide containing a site for neutrophil elastases are as follows:

```
(DABCYL)2-Lys-Ala-Ala-Pro-Val (SEQ ID NO: 6)-(5-
FAM)

(DABCYL)2-Arg-Ala-Ala-Pro-Val (SEQ ID NO: 7)-(5-
FAM)

(DABCYL)2-GABA-Ala-Ala-Pro-Val (SEQ ID NO: 8)-(5-
FAM)

DABCYL-Ala-Ala-Pro-Val-Glu (SEQ ID NO: 9)-(5-FAM)2

DABCYL-Ala-Ala-Pro-Val-Asp (SEQ ID NO: 10)-(5-
FAM)2

(DABCYL)2-Lys-Ala-Ala-Pro-Val-Glu (SEQ ID NO: 11)-
(5-FAM)2

(DABCYL)2-Arg-Ala-Ala-Pro-Val-Glu (SEQ ID NO: 12)-
(5-FAM)2

(DABCYL)2-GABA-Ala-Ala-Pro-Val-Glu (SEQ ID NO:
13)-(5-FAM)2

(DABCYL)2-Lys-Ala-Ala-Pro-Val-Asp (SEQ ID NO: 14)-
(5-FAM)2

(DABCYL)2-Arg-Ala-Ala-Pro-Val-Asp (SEQ ID NO: 15)-
(5-FAM)2

(DABCYL)2-GABA-Ala-Ala-Pro-Val-Asp (SEQ ID NO:
16)-(5-FAM)2

(DABCYL)2-Lys-Ala-Ala-Ala-Ala (SEQ ID NO: 17)-(5-
FAM)

(DABCYL)2-Arg-Ala-Ala-Ala-Ala (SEQ ID NO: 18)-(5-
FAM)

(DABCYL)2-GABA-Ala-Ala-Ala-Ala (SEQ ID NO: 19)-(5-
FAM)

DABCYL-Ala-Ala-Ala-Ala-Glu (SEQ ID NO: 20)-(5-
FAM)2

DABCYL-Ala-Ala-Ala-Ala-Asp (SEQ ID NO: 21)-(5-
FAM)2

(DABCYL)2-Lys-Ala-Ala-Ala-Ala-Glu (SEQ ID NO:
22)-(5-FAM)2
```

-continued (DABCYL)2-Arg-Ala-Ala-Ala-Ala-Glu (SEQ ID NO: 23)-(5-FAM)2

(DABCYL)2-GABA-Ala-Ala-Ala-Ala-Glu (SEQ ID NO: 24)-(5-FAM)2

(DABCYL)2-Lys-Ala-Ala-Ala-Ala-Asp (SEQ ID NO: 25)-(5-FAM)2

(DABCYL)2-Arg-Ala-Ala-Ala-Ala-Asp (SEQ ID NO: 26)-(5-FAM)2

(DABCYL)2-GABA-Ala-Ala-Ala-Ala-Asp (SEQ ID NO: 27)-(5-FAM)2

The quencher is constrained by two primary requirements: compatibility with the protease (e.g. shape) and spectral characteristics (e.g. compatibility with the fluorophore) (limited success has been achieved using xanthene dyes as quenchers (5-FAM and rhodamine).

The antibody binds to the protease, or to the peptide substrate, and stops the cleavage reaction. In one embodiment, the antibody is an anti-neutrophil elastase antibody. In other embodiments, SERPINS are used to stop the cleavage reaction. Examples of SERPINS for use in accordance with the subject invention include, but are not limited to, SERPINA1 and SERPINB1. Additionally, adding chemicals such as EDTA into the stop and read chamber can assure complete stop.

This device provides a method of rapid quantification of protease activities in wound tissue. In one embodiment in which the peptide cleavage site is neutrophil elastase, the incubation time of the proteolysis reaction is around 10 minutes. Therefore, by using this device, the caregiver is able to quantify the level of protease activity in the actual wound in a short time and give necessary treatment immediately.

Example 2—Biological Samples

The devices and methods of the subject invention can be used to detect and/or quantify the presence, quantity, and/or activity of neutrophil elastase in a variety of biological samples. The devices according to the subject can be used to assay various samples as follows:

A. Wound Fluids (Chronic Wounds)
Obtained by:
1. Swab
2 Vac
3. Bandage/dressing
4. Capillary/pipette
5. Syringe
6. Test run in-vivo in the wound
7. Tissue biopsy
B. Tear Fluid
Obtained by:
1. Wicking paper/material
2. Capillary/pipette
3. Syringe
C. Vaginal Fluid
Obtained by:
1. Swab
2. Capillary/pipette
3. Panty liner
4. Tampon
5. Wicking paper/material
6. Syringe
7. Tissue biopsy
D. Oral fluids
1. Saliva
Obtained by:
a. Patient spitting into receptacle
b. Cheek swab
c. Capillary/pipette
d. Wicking paper/material
e. Syringe
f. Tissue biopsy
2. Crevicular Fluid (periodontal space)
Obtained by:
a. Syringe
b. Capillary/pipette
c. Collected scrapings
d. Wicking paper/material
e. Swab
f. Tissue biopsy
E. Nasal
Obtained by:
1. Collection of naturally evacuated fluids (runny nose)
2. Forced evacuation (blowing one's nose) into receptacle
3. Swab
4. Flushing
5. Capillary/pipette
6. Wicking paper/material
7. Syringe
8. Tissue biopsy
F. Throat
Obtained by:
1. Forced evacuation (coughing) into/onto receptacle
2. Swab
3. Flushing-gargling-spitting
4. Capillary/pipette
5. Wicking paper/material
6. Syringe
7. Tissue biopsy
G. Otological (ear)
Obtained by:
1. Swab
2. Flushing
3. Capillary/pipette
4. Wicking paper/material
5. Syringe
6. Tissue biopsy
H. Axilla
Obtained by:
1. Swab
2. Flushing
3. Capillary/pipette
4. Wicking paper/material
5. Syringe
6. Clothing (sweat)
7. Tissue biopsy
I. Pulmonary (Lung)
Obtained by:
1. Forced evacuation (coughing) into/onto receptacle
2. Swab
3. Capillary/pipette
4. Wicking paper/material
5. Syringe
6. Vac
7. Tissue biopsy
J. Cyst
Obtained by:
1. Swab
2. Capillary/pipette 3. Wicking paper/material
4. Syringe
5. Vac
6. Tissue biopsy
K. Synovial Fluid/Connective Tissue
   Obtained by:
1. Swab
2. Capillary/pipette
3. Wicking paper/material
4. Syringe
5. Vac
6. Tissue biopsy
L. Urological
   Urethra
M. Feces
N. Urine
O. Blood
P. Semen
Q. Vomit All patents, patent applications, provisional applications, and publications referred to or cited herein, supra or infra, are incorporated by reference in their entirety, including all figures and tables, to the extent they are not inconsistent with the explicit teachings of this specification. It should be understood that the examples and embodiments described herein are for illustrative purposes only and that various modifications or changes in light thereof will be suggested to persons skilled in the art and are to be included within the spirit and purview of this application.

We claim:

1. A method for detection of neutrophil elastase in a fluid from a chronic wound wherein said method comprises the following steps:
   a) providing, in a self-contained unit, a single-peptide substrate comprising GABA-Ala-AlaAla-Ala- (SEQ ID NO: 19), to which is attached a fluorescing dye and a quencher, wherein the fluorescing dye is (5-F AM) and the quencher is DABCYL, and wherein the fluorescing dye and the quencher are in sufficiently close proximity on the substrate such that the quencher quenches the fluorescence of the fluorescing dye, and wherein the fluorescing dye and the quencher are separated by the substrate such that, if the neutrophil elastase cleaves the substrate, the fluorescing dye is separated from the quencher,
   b) collecting a sample of chronic wound fluid from a patient,
   c) in the self-contained unit, contacting the substrate with the fluid within 30 minutes after collection of said fluid for a period of time sufficient to permit substrate cleavage to occur if there is neutrophil elastase present in the fluid; and
   d) detecting any fluorescence, wherein the presence of neutrophil elastase in the fluid is indicated by fluorescence.

2. The method, according to claim 1, wherein results are obtained in less than 1 0 minutes after the sample is collected.

3. The method, according to claim 1, wherein said method gives a quantitative indication of the amount of neutrophil elastase present in the fluid.

4. The method, according to claim 1, wherein the contacting step is carried out in the same container as the fluorescence detection step.

5. The method, according to claim 1, wherein the fluid is collected in a hollow straw and absorbed onto a swab therein,
   a solution containing the substrate is then added to the hollow straw, travels through the hollow straw, and contacts the swab containing the fluid, and
   the swab containing the fluid and the substrate is inserted into another chamber in which the fluorescence detection step takes place.

6. The method, according to claim 1, which utilizes only the self-contained unit and a means for causing the fluorescing dye to fluoresce.

7. The method, according to claim 1, wherein the method is conducted bedside.

* * * * *

SEQUENCE LISTING

```
<160> NUMBER OF SEQ ID NOS: 27

<210> SEQ ID NO 1
<211> LENGTH: 4
<212> TYPE: PRT
<213> ORGANISM: Artificial Sequence
<220> FEATURE:
<223> OTHER INFORMATION: cleavage site for neutrophil elastases with a
      dabcyl quencher at the N terminal and 5-FAM at the C-terminal

<400> SEQUENCE: 1

Ala Ala Pro Val
1

<210> SEQ ID NO 2
<211> LENGTH: 4
<212> TYPE: PRT
<213> ORGANISM: Artificial Sequence
<220> FEATURE:
<223> OTHER INFORMATION: fluorophore-labeled peptides containing a
      cleavage site for neutrophil elastases

<400> SEQUENCE: 2

Ala Ala Pro Val
1

<210> SEQ ID NO 3
<211> LENGTH: 4
<212> TYPE: PRT
<213> ORGANISM: Artificial Sequence
<220> FEATURE:
<223> OTHER INFORMATION: fluorophore-labeled peptides containing a
      cleavage site for neutrophil elastases

<400> SEQUENCE: 3

Ala Ala Ala Ala
1

<210> SEQ ID NO 4
<211> LENGTH: 8
<212> TYPE: PRT
<213> ORGANISM: Artificial Sequence
<220> FEATURE:
<223> OTHER INFORMATION: fluorophore-labeled peptides containing a
      cleavage site for neutrophil elastases

<400> SEQUENCE: 4

Ala Ala Ala Ala Ala Ala Ala Ala
1               5
```

```
<210> SEQ ID NO 5
<211> LENGTH: 4
<212> TYPE: PRT
<213> ORGANISM: Artificial Sequence
<220> FEATURE:
<223> OTHER INFORMATION: cleavage site for neutrophil elastases with a
      dabcyl quencher at the N terminal and 5-FAM at the C-terminal

<400> SEQUENCE: 5

Ala Ala Ala Ala
1

<210> SEQ ID NO 6
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 6

Lys Ala Ala Pro Val
1               5

<210> SEQ ID NO 7
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 7

Arg Ala Ala Pro Val
1               5

<210> SEQ ID NO 8
<211> LENGTH: 4
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 8

Ala Ala Pro Val
1

<210> SEQ ID NO 9
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 9

Ala Ala Pro Val Glu
1               5

<210> SEQ ID NO 10
<211> LENGTH: 5
<212> TYPE: PRT
<213> ORGANISM: Artificial Sequence
```

```
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 10

Ala Ala Pro Val Asp
1               5

<210> SEQ ID NO 11
<211> LENGTH: 6
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 11

Lys Ala Ala Pro Val Glu
1               5

<210> SEQ ID NO 12
<211> LENGTH: 6
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 12

Arg Ala Ala Pro Val Glu
1               5

<210> SEQ ID NO 13
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 13

Ala Ala Pro Val Glu
1               5

<210> SEQ ID NO 14
<211> LENGTH: 6
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 14

Lys Ala Ala Pro Val Asp
1               5

<210> SEQ ID NO 15
<211> LENGTH: 6
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal
```

```
<400> SEQUENCE: 15

Arg Ala Ala Pro Val Asp
1               5

<210> SEQ ID NO 16
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 16

Ala Ala Pro Val Asp
1               5

<210> SEQ ID NO 17
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 17

Lys Ala Ala Ala Ala
1               5

<210> SEQ ID NO 18
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 18

Arg Ala Ala Ala Ala
1               5

<210> SEQ ID NO 19
<211> LENGTH: 4
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 19

Ala Ala Ala Ala
1

<210> SEQ ID NO 20
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 20

Ala Ala Ala Ala Glu
1               5
```

```
<210> SEQ ID NO 21
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 21

Ala Ala Ala Ala Asp
1               5

<210> SEQ ID NO 22
<211> LENGTH: 6
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 22

Lys Ala Ala Ala Ala Glu
1               5

<210> SEQ ID NO 23
<211> LENGTH: 6
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 23

Arg Ala Ala Ala Ala Glu
1               5

<210> SEQ ID NO 24
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 24

Ala Ala Ala Ala Glu
1               5

<210> SEQ ID NO 25
<211> LENGTH: 6
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 25

Lys Ala Ala Ala Ala Asp
1               5

<210> SEQ ID NO 26
<211> LENGTH: 6
<212> TYPE: PRT
<213> ORGANISM: Artificial Sequence
```

```
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 26

Arg Ala Ala Ala Ala Asp
1               5

<210> SEQ ID NO 27
<211> LENGTH: 5
<212> TYPE: PRT
<213> ORGANISM: Artificial Sequence
<220> FEATURE:
<223> OTHER INFORMATION: cleavage site for neutrophil elastases with
      dabcyl quencher(s) at the N terminal and 5-FAM(s) at the
      C-terminal

<400> SEQUENCE: 27

Ala Ala Ala Ala Asp
1               5
```